United States Patent
Crowe

(10) Patent No.: US 11,957,520 B1
(45) Date of Patent: Apr. 16, 2024

(54) SURGICAL HEADLAMP ASSEMBLY

(71) Applicants: Brian Crowe, Saunemin, IL (US); Ryan Pizinger, Plainfield, IL (US)

(72) Inventor: Brian Crowe, Saunemin, IL (US)

(73) Assignee: Brian Crowe, Saunemin, IL (US)

( * ) Notice: Subject to any disclaimer, the term of this patent is extended or adjusted under 35 U.S.C. 154(b) by 0 days.

(21) Appl. No.: 17/721,649

(22) Filed: Apr. 15, 2022

Related U.S. Application Data

(60) Provisional application No. 63/178,396, filed on Apr. 22, 2021.

(51) Int. Cl.
*A61B 90/30* (2016.01)
*A61B 90/50* (2016.01)

(52) U.S. Cl.
CPC .............. *A61B 90/30* (2016.02); *A61B 90/50* (2016.02); *A61B 2090/309* (2016.02); *A61B 2090/502* (2016.02)

(58) Field of Classification Search
CPC ... A61B 90/30; A61B 90/50; A61B 2090/309; A61B 2090/502
USPC .................................................. 362/804, 105
See application file for complete search history.

(56) References Cited

U.S. PATENT DOCUMENTS

| | | | |
|---|---|---|---|
| 2,893,379 A * | 7/1959 | Springer | A61B 3/0008 600/184 |
| 3,285,242 A | 11/1966 | Wallace | |
| 5,637,863 A | 6/1997 | Sanborn et al. | |
| 6,896,389 B1 | 5/2005 | Paul | |
| 7,008,074 B1 | 3/2006 | Halm | |
| 7,192,151 B2 | 3/2007 | Clupper et al. | |
| 7,370,991 B1 | 5/2008 | Ellis-Fant | |
| 8,653,702 B2 | 2/2014 | Saleh | |
| 8,851,709 B2 | 10/2014 | Feinbloom et al. | |
| 8,899,774 B2 | 12/2014 | Strong et al. | |
| 8,900,138 B2 | 12/2014 | Horvath | |
| 9,062,833 B2 | 6/2015 | Nakamura | |
| 9,851,080 B2 | 12/2017 | Wilt et al. | |
| 10,724,716 B2 | 7/2020 | Neeley et al. | |
| 10,842,002 B2 | 11/2020 | Chang | |
| 10,869,733 B2 | 12/2020 | Learn | |
| 2006/0285315 A1 | 12/2006 | Tufenkjian | |
| 2008/0144332 A1 | 6/2008 | Medinis | |

(Continued)

*Primary Examiner* — Laura K Tso

(57) ABSTRACT

A surgical headlamp assembly which can be remotely actuated at a wearer's chest and is suitable for surgical applications may include a headpiece. The headpiece may be sizable and configurable for placement on the head of a wearer. A lamp may be provided on the headpiece. The lamp may include at least one light source. At least one battery may be provided on the headpiece. The lamp may electrically interface with the battery. A remote lamp control module may operationally interface with the battery and the lamp. The lamp control module may be configured to control emission of a light beam from the lamp. The remote lamp control module may be suspendable from the headpiece and deployable in front of the chest of the wearer. In typical application of the surgical headlamp assembly, the lamp control module may be worn on the chest of the wearer. The wearer may manipulate the lamp control module to energize and adjust the illumination intensity of the light beam without interruption of the surgical procedure and without the need to use the surgeon's fingers.

20 Claims, 7 Drawing Sheets

(56) References Cited

U.S. PATENT DOCUMENTS

| | | | |
|---|---|---|---|
| 2008/0316733 A1* | 12/2008 | Spartano | F21V 14/065 362/105 |
| 2009/0323317 A1* | 12/2009 | Spartano | F21V 23/0414 362/105 |
| 2015/0003048 A1 | 1/2015 | Chang | |
| 2015/0349544 A1* | 12/2015 | Lutz | A61B 1/00029 433/29 |
| 2016/0146443 A1* | 5/2016 | Steiner | F21V 14/065 362/105 |
| 2017/0211759 A1* | 7/2017 | Qiu | F21V 21/084 |
| 2018/0051870 A1 | 2/2018 | Ayala et al. | |
| 2018/0296079 A1 | 10/2018 | Orringer et al. | |
| 2019/0036992 A1 | 1/2019 | Stewart et al. | |

* cited by examiner

SURGICAL HEADLAMP ASSEMBLY

CROSS-REFERENCE TO RELATED APPLICATIONS

This application claims the benefit of U.S. Provisional Patent Application No. 63/178,396, filed on Apr. 22, 2021, which is incorporated by reference herein in its entirety.

FIELD OF THE INVENTION

The present invention relates generally to headlamps, and more particularly, to a surgical headlamp assembly which can be remotely actuated by a wearer at the wearer's chest and is suitable for surgical applications.

BACKGROUND OF THE INVENTION

Adequate illumination is necessary in a wide variety of contexts. For example, some types of work may require focused illumination of a small area in front of the worker. This type of illumination may be required in such applications as surgery, dentistry, and jewelry repair.

A surgical operating room may be equipped with overhead lighting which may be recessed in the ceiling of the room. Adjustable surgical lamps may be mounted on lamp support arms beneath the ceiling. The adjustable surgical lamps may be adjusted in location and position to adjust the lighting direction and intensity of the light beams emitted by the lamps onto the surgical field.

During a surgical procedure, the surgeon is required to maintain sterile hands. Therefore, conventional surgical lamps may include sterilizable handles and/or handle covers which enable personnel to adjust the beams of light projected by the lamps to illuminate a desired area without the need for the surgeon to contaminate the surgeon's hands. These handles or handle covers may be replaced between surgical procedures.

In some surgical applications, ambient lighting may be inadequate to illuminate the surgical field to the satisfaction of the surgeon. Additionally, shadows cast by the surgeon, surgical personnel and/or equipment may further impair visibility of the surgical field. Accordingly, a headlamp may be deployed on the head of the surgeon to illuminate the surgical field while freeing the hands of the surgeon to manipulate surgical equipment.

Conventional surgical headlamps may include an incandescent bulb mounted on a headpiece. The headpiece is worn on the head of the surgeon with the bulb positioned in front of the surgeon's forehead. A common limitation of using an incandescent bulb as the light source, however, is that significant heat may be generated by the bulb. Since the surgeon is dressed in a full-length surgical gown with long sleeves during the procedure, the additional heat generated by the bulb may cause the surgeon to become excessively hot and uncomfortable, particularly in the case of long surgical procedures.

Traditional surgical headlamp designs may require that the light bulb of the headpiece be connected to an external power source. However, the remote location of the external power source may limit freedom of the surgeon to move with respect to the patient. Moreover, the control button or switch for the headlamp may be located on the headlamp itself. Accordingly, if the surgeon desires to adjust the angle or light intensity of the light beam emitted by the light bulb, or desires to turn the headlamp off, the surgeon may be required to touch the controls for the headlamp during surgery. This drawback may compromise the sterility of the surgeon's hands during the procedure. Additionally, the surgeon may be required to interrupt the surgical procedure to make the adjustments.

In the field of orthopedic surgery, some procedures may be performed in a dark operating room. Tedious surgical work, such as tying stitches, for example, may require a concentrated source of light. Accordingly, surgical headlamps may be ideal for facilitating adequate illumination and visualization of the surgical field.

Accordingly, there is need for a surgical headlamp assembly which can be remotely actuated at a wearer's chest and is suitable for surgical applications.

SUMMARY OF THE INVENTION

The present invention is directed to a surgical headlamp assembly which can be remotely actuated at a wearer's chest and is suitable for surgical applications. An illustrative embodiment of the surgical headlamp assembly may include a headpiece. The headpiece may be sizable and configurable for placement on the head of a wearer. A lamp may be provided on the headpiece. The lamp may include at least one light source. At least one battery may be provided on the headpiece. The lamp may electrically interface with the battery. A remote lamp control module may operationally interface with the battery and the lamp. The lamp control module may be configured to control emission of a light beam from the lamp. The remote lamp control module may be suspendable from the headpiece and deployable in front of the chest of the wearer. In typical application of the surgical headlamp assembly, the lamp control module may be worn on the chest of the wearer. The wearer may manipulate the lamp control module to energize and adjust the illumination intensity of the light beam without interruption of the surgical procedure and without the need to use the surgeon's fingers.

In an illustrative implementation of the invention, a surgical headlamp assembly which can be remotely actuated by a wearer at the wearer's chest and is suitable for surgical applications may include a headpiece. The headpiece may be sizable and configurable for placement on the head of the wearer. The headpiece may be selectively adjustable in size to accommodate the head of the wearer. A lamp may be provided on the headpiece. The lamp may include at least one light source. A battery pack may be provided on the headpiece. The battery pack may include at least one battery. The lamp may electrically interface with the battery pack. A remote lamp control module may operationally interface with the battery pack and the headpiece. The remote lamp control module may be suspendable from the headpiece and deployable in front of the chest of the wearer. The lamp control module may be configured to control emission of a light beam from the lamp. In typical application of the surgical headlamp assembly, the lamp control module may be worn on the chest of the user. The user may manipulate the lamp control module to energize and adjust the illumination intensity of the light beam without interruption of the surgical procedure and without the need to use the surgeon's fingers.

In a second aspect, the headpiece may include a plurality of headpiece straps.

In another aspect, the plurality of headpiece straps may include a pair of lateral strap members and an upper strap member.

In another aspect, each of the lateral strap members and the upper strap member may be selectively adjustable.

In another aspect, each lateral strap member may include a front lateral strap, a rear lateral strap and a lateral strap adjuster between the front lateral strap and the rear lateral strap.

In another aspect, the upper strap member may include a front upper strap, a rear upper strap and an upper strap adjuster between the front upper strap and the rear upper strap.

In another aspect, a rear strap loop may connect the rear lateral straps of the lateral strap members.

In another aspect, the headpiece may include a lamp mount panel, and the lamp may be supported by the lamp mount panel.

In another aspect, the lateral strap members and the upper strap member of the headpiece may be attached to the lamp mount panel.

In another aspect, a pair of side strap member slots may extend through the lamp mount panel, and the front lateral strap of each lateral strap member may extend through the corresponding side strap member slot.

In another aspect, an upper strap member slot may extend through the lamp mount panel between the side strap member slots, and the front upper strap may loop through the upper strap member slot.

In another aspect, the battery pack may be disposed behind and in spaced-apart relationship to the lamp mount panel, and the lateral strap members and the upper strap member of the headpiece may be secured to the battery pack.

In another aspect, at least one strap securement band may secure the lateral strap members and the upper strap member to the battery pack.

In another aspect, the lamp may include a lamp housing, and the at least one light source may be disposed in the lamp housing.

In another aspect, the at least one light source may include at least one LED.

In another aspect, a lens housing may extend from the lamp housing, and at least one lens may be disposed in the lens housing.

In another aspect, a manual lamp button may be provided on the lamp housing to facilitate manual operation of the at least one light source.

In another aspect, the lamp housing may emit a focusable light beam which can be conical or straight.

In another aspect, a light beam adjustment control may be provided on the lens housing to adjust the width of the light beam emitted from the lens housing.

In another aspect, the lamp may be selectively adjustable at a selected angle with respect to the headpiece.

In another aspect, at least one lamp hinge may pivotally attach the lamp to the headpiece.

In another aspect, the battery pack may include a battery pack housing and at least one battery compartment in the battery pack housing, and the battery may be insertable in the battery compartment.

In another aspect, the lamp control module may be deployable in a suspended configuration from the headpiece.

In another aspect, battery wiring may connect the lamp to the battery pack.

In another aspect, control wiring may connect the lamp control module to the lamp.

In another aspect, the battery wiring and the control wiring may trail along one of the lateral strap members of the headpiece.

In another aspect, the control wiring may extend between the rear strap loop and the battery pack housing of the battery pack.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a surgical headlamp assembly which can be remotely actuated by a wearer at the wearer's chest and is suitable for surgical applications.

Figure 3:
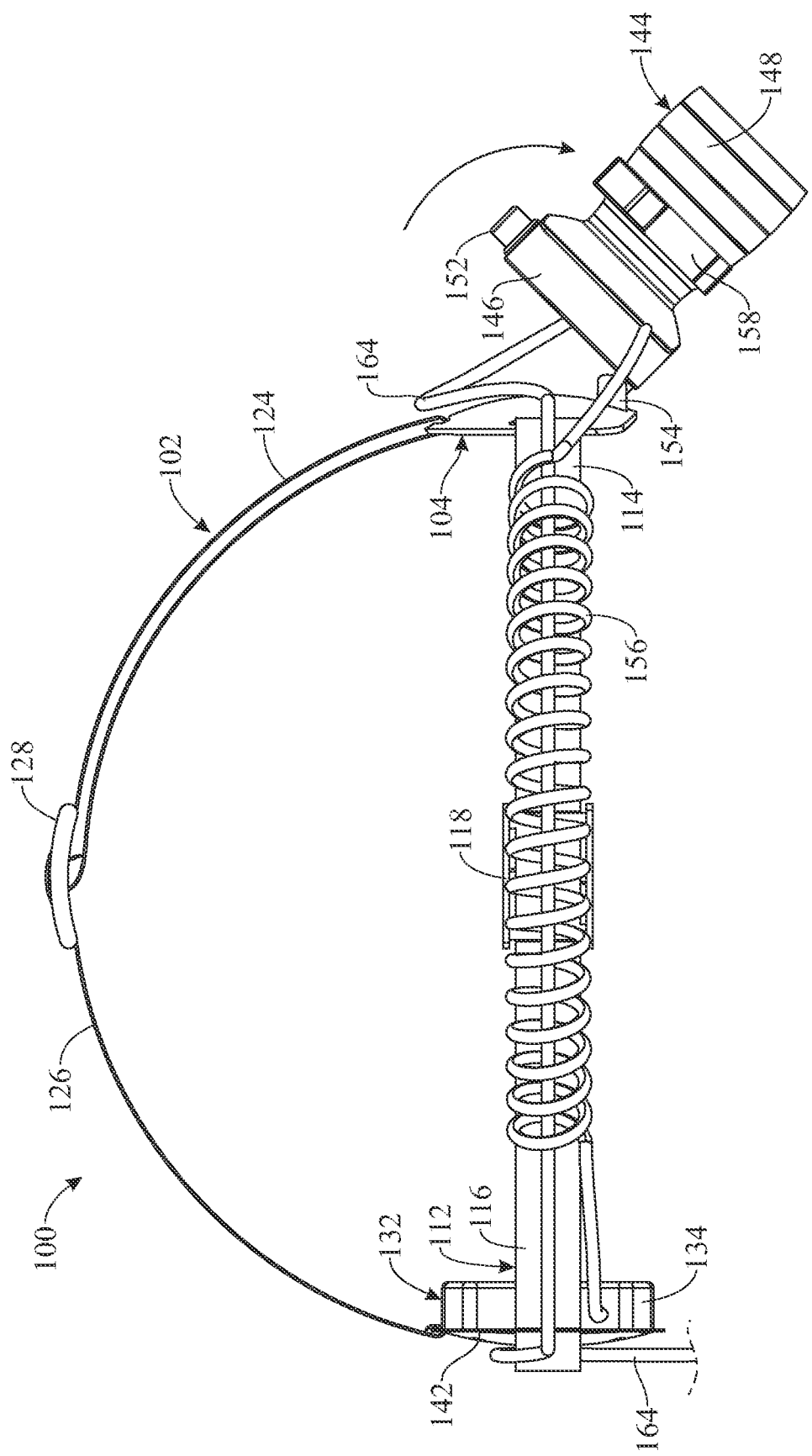
FIG. 3 presents a side view of the illustrative surgical headlamp assembly, with the lamp disposed in a downwardly-tilted position relative to the headpiece.
Figure 4:
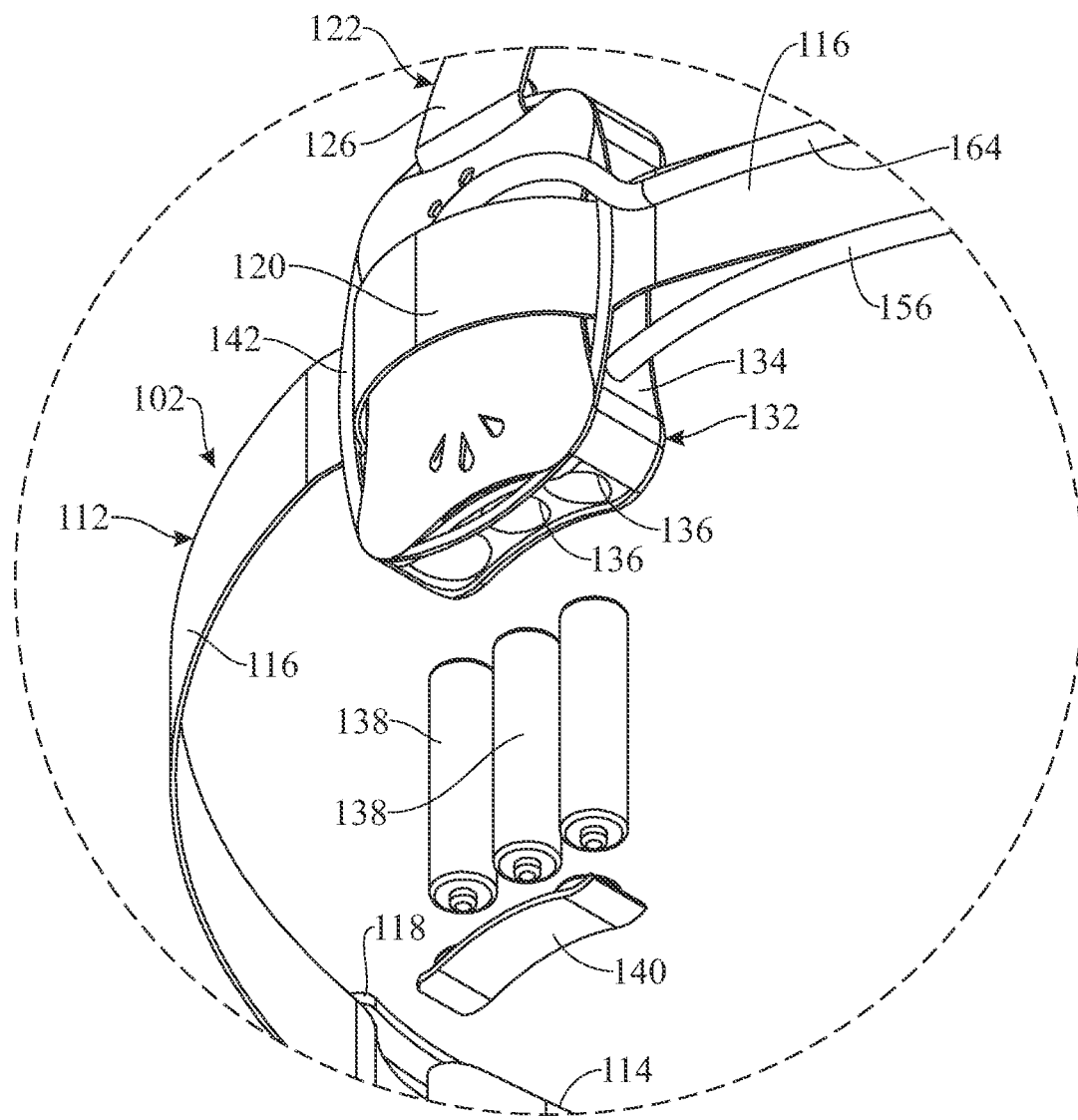
FIG. 4 presents an enlarged, exploded perspective view of a typical battery pack of the illustrative surgical headlamp assembly, with multiple batteries removed from respective battery compartments in the battery pack.
Figure 5:
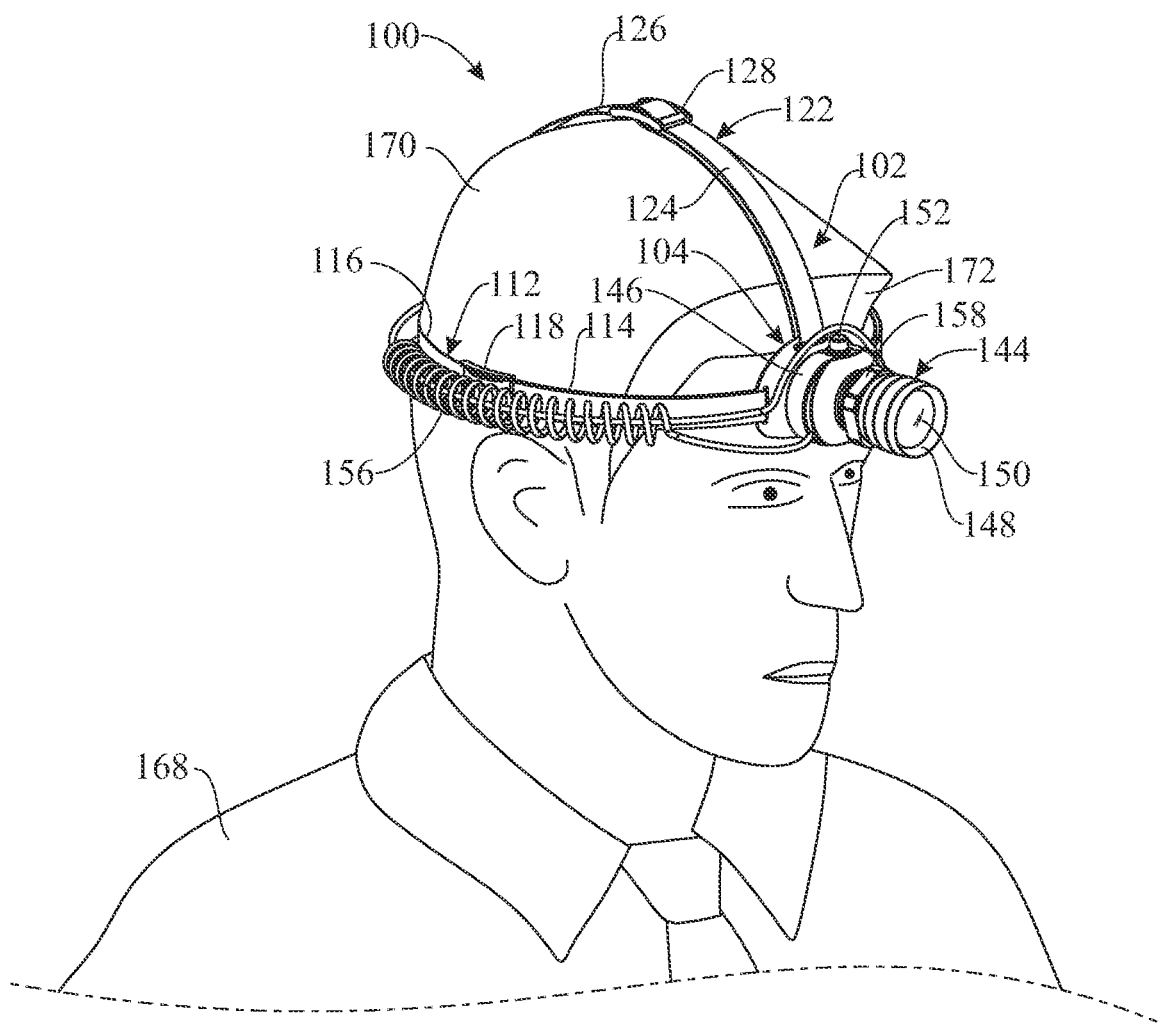
FIG. 5 presents a front perspective view of the illustrative surgical headlamp assembly, donned on the head of a wearer in typical application of the assembly.
Figure 6:
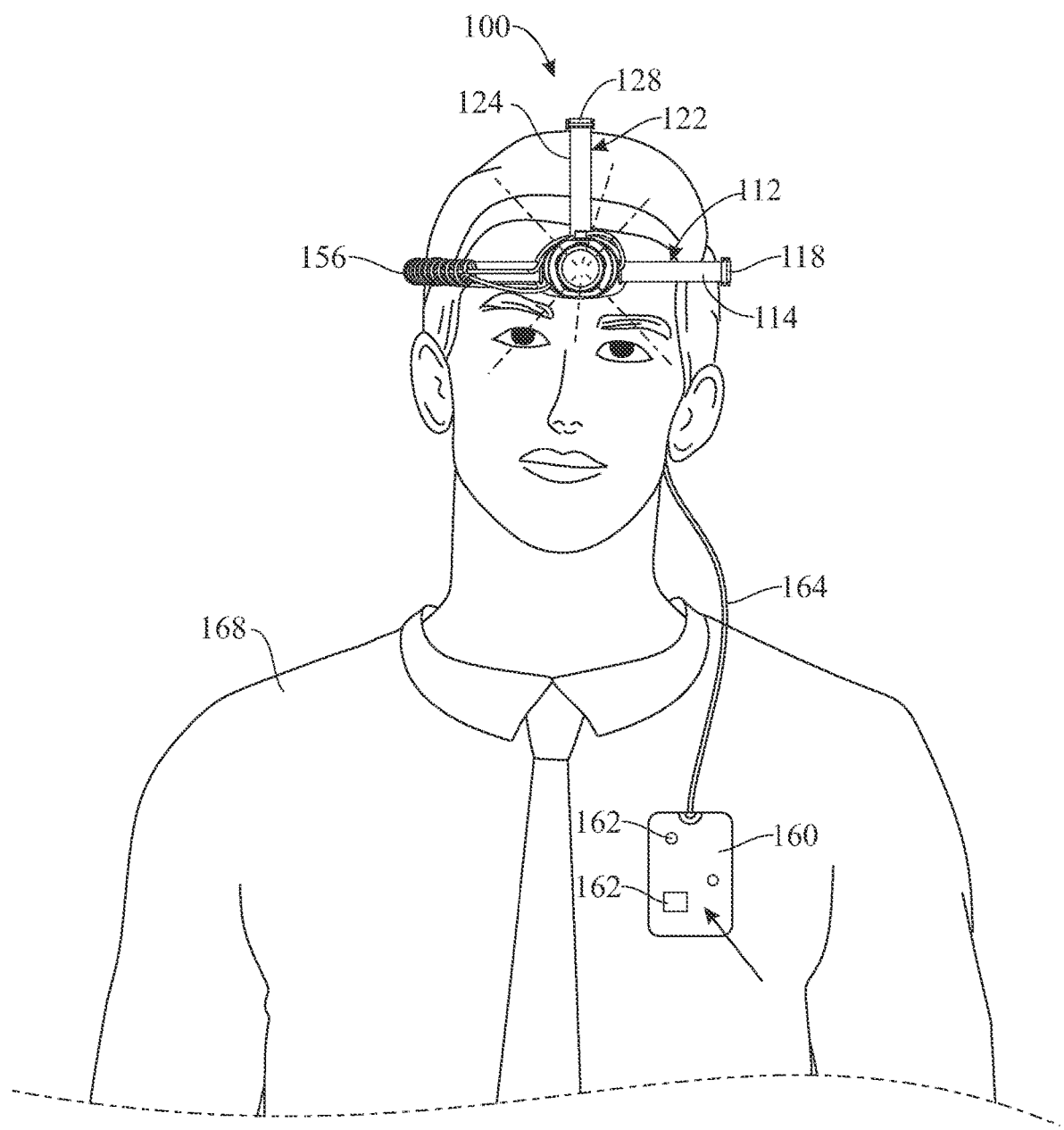
FIG. 6 presents a front view of the surgical headlamp assembly illustrated in FIG. 5, with the lamp control module of the assembly deployed in front of the chest of the wearer.

Referring initially to FIGS. 1-7, a surgical headlamp assembly, hereinafter headlamp assembly 100, is illustrated in accordance with an exemplary embodiment of the present invention. As shown for instance in FIG. 1, the headlamp assembly 100 may include a headpiece 102. As illustrated in FIGS. 5 and 6, the headpiece 102 may be sizable and configurable for placement on the head 170 of a wearer 168. In some applications, the wearer 168 may be a surgeon, for example and without limitation. A lamp 144 may be provided on the headpiece 102. The lamp 144 may include at least one light source (not illustrated).

Figure 7:
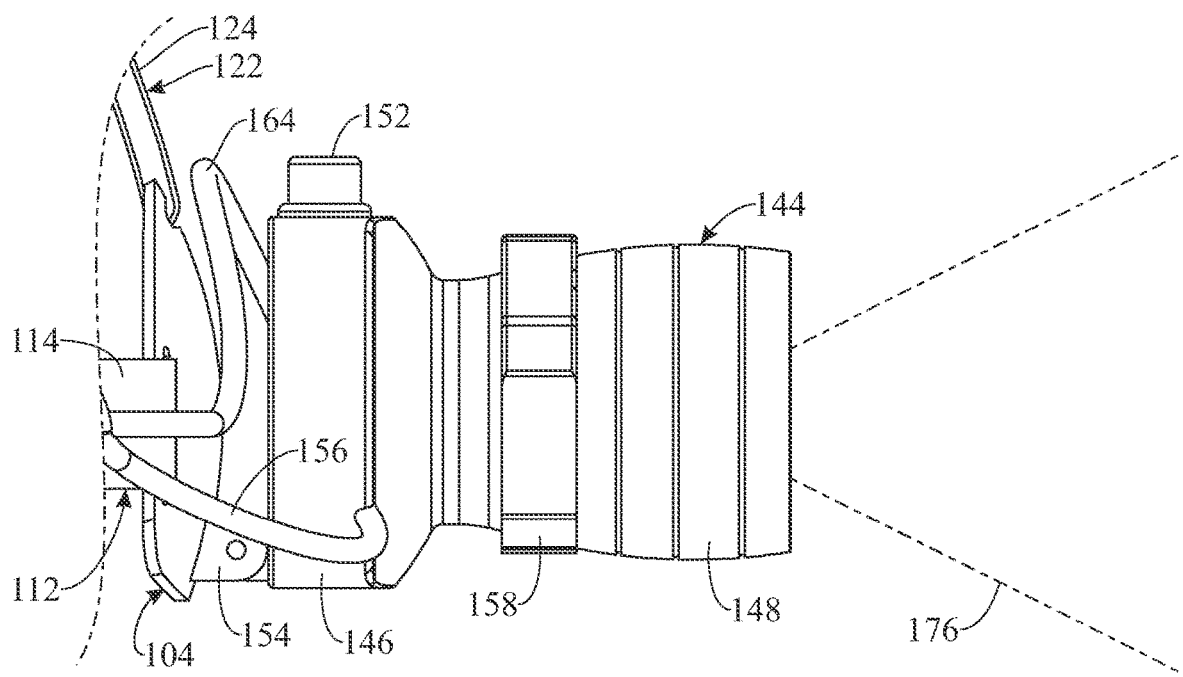
FIG. 7 presents a pair of side views, respectively, of a typical lamp of the surgical headlamp assembly, more particularly illustrating a conical configuration (upper view) and a straight configuration (lower view) of the light beam emitted from the lens housing of the assembly.
Figure 7:
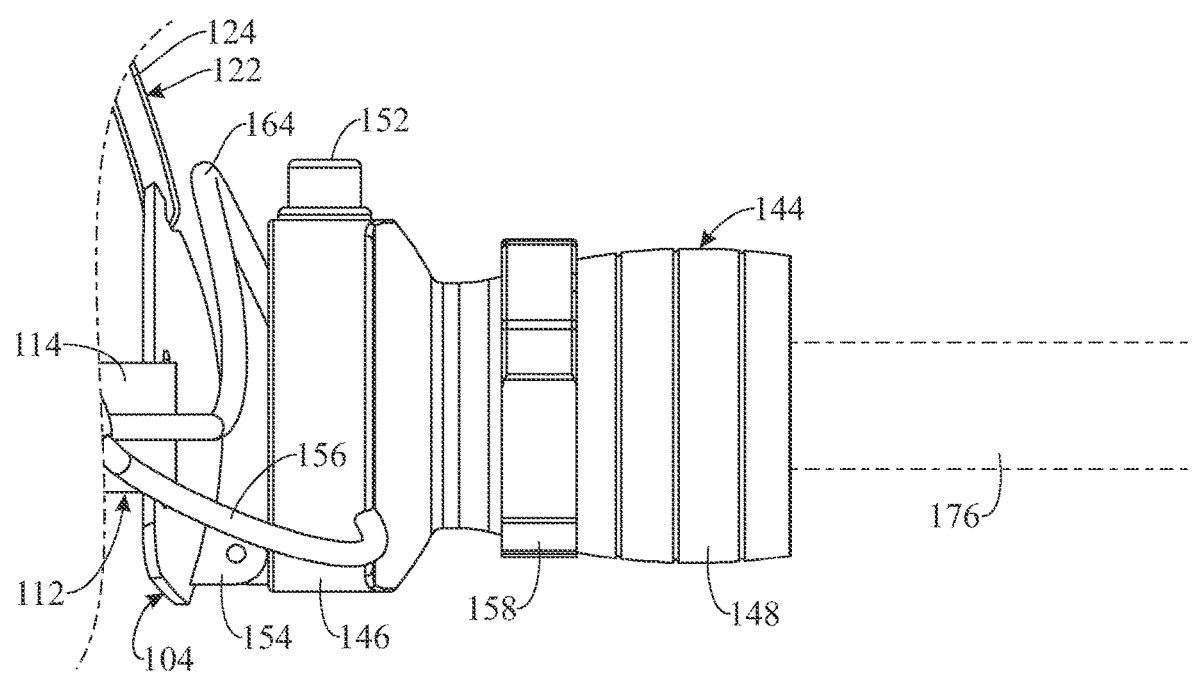

At least one battery 138 (FIG. 4) may be provided on the headpiece 102. The lamp 144 may electrically interface with the battery 138. A remote lamp control module 160 may operationally interface with the battery 138 and the headpiece 102. The remote lamp control module 160 may include lamp controls 162. As illustrated in FIG. 7, the lamp control module 160 may be configured to control emission of a light beam 176 from the lamp 144. The lamp controls 162 may control such parameters as the on/off status and the illumination intensity, for example and without limitation, of the light beam 176 emitted by the lamp 144. In typical application of the surgical headlamp assembly 100, which will be hereinafter described, the lamp control module 160 may be worn on or over the chest of the wearer 168, as illustrated in FIG. 6. The wearer 168 may manipulate the lamp control module 160 to energize and adjust the illumination intensity of the light beam 176 without interruption of the surgical procedure and without the need to use the surgeon's fingers. In some embodiments, the remote lamp control module 160 may be fitted with a clip (not illustrated) to facilitate attachment of the remote lamp control module 160 to the shirt of the wearer 168.

In some embodiments, the remote lamp control module 160 may include a capacitor switch (not illustrated). A capacitor switch is a type of touch-controlled electrical switch that operates by measuring change in capacitance. When a capacitor switch is touched, this electrical charge disturbs the electrical charge of the switch, thus causing a change in capacitance. The capacitor switch is thus ideal for a surgical application in which a surgeon desires to actuate the switch without use of the hands.

A battery pack 132 may be provided on the headpiece 102. As illustrated in FIG. 4, the battery pack 132 may include at least one battery 138. The lamp 144 may electrically interface with the battery pack 132. The remote lamp control module 160 may operationally interface with the battery pack 132 and the lamp 144, typically as will be hereinafter described.

The headpiece 102 may have any design which is suitable for secure placement on the head 170 of the wearer 168. As illustrated in FIGS. 1-4, in some embodiments, the headpiece 102 may include a plurality of headpiece straps 112, 122. The headpiece straps 112, 122 may include a pair of lateral strap members 112 and an upper strap member 122. In some embodiments, the lateral strap members 112 and the upper strap member 122 may be elastic.

In some embodiments, each lateral strap member 112 and the upper strap member 122 may be selectively adjustable according to the knowledge of those skilled in the art. Accordingly, each lateral strap member 112 may include a front lateral strap 114. A rear lateral strap 116 may extend from the front lateral strap 114. A lateral strap adjuster 118 may connect the front lateral strap 114 to the rear lateral strap 116. The length of the lateral strap member 112 may be selectively adjusted by pulling or pushing the front lateral strap 114 and/or the rear lateral strap 116 through the lateral strap adjuster 118.

The upper strap member 122 of the headpiece 102 may include a front upper strap 124. A rear upper strap 126 may extend from the front upper strap 124. An upper strap adjuster 128 may connect the front upper strap 124 to the rear upper strap 126. The length of the upper strap member 122 may be selectively adjusted by pulling or pushing the front upper strap 124 and/or the rear upper strap 126 through the upper strap adjuster 128.

Figure 2:
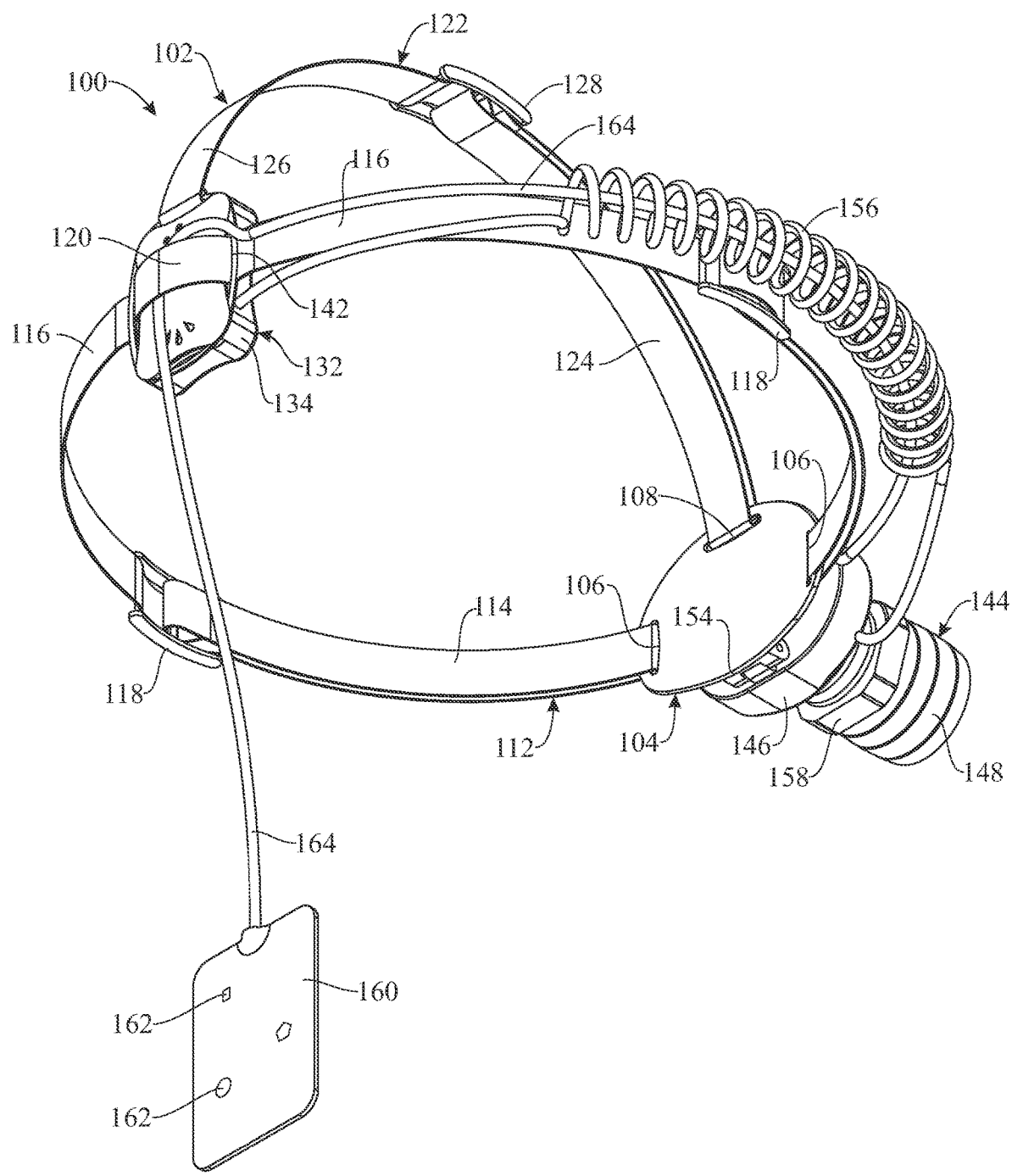
FIG. 2 presents a rear perspective view of the illustrative surgical headlamp assembly.

As illustrated in FIG. 2, in some embodiments, a rear strap loop 120 may connect the rear lateral straps 116 of the lateral strap members 112. The purpose of the rear strap loop 120 will be hereinafter described.

Figure 1:
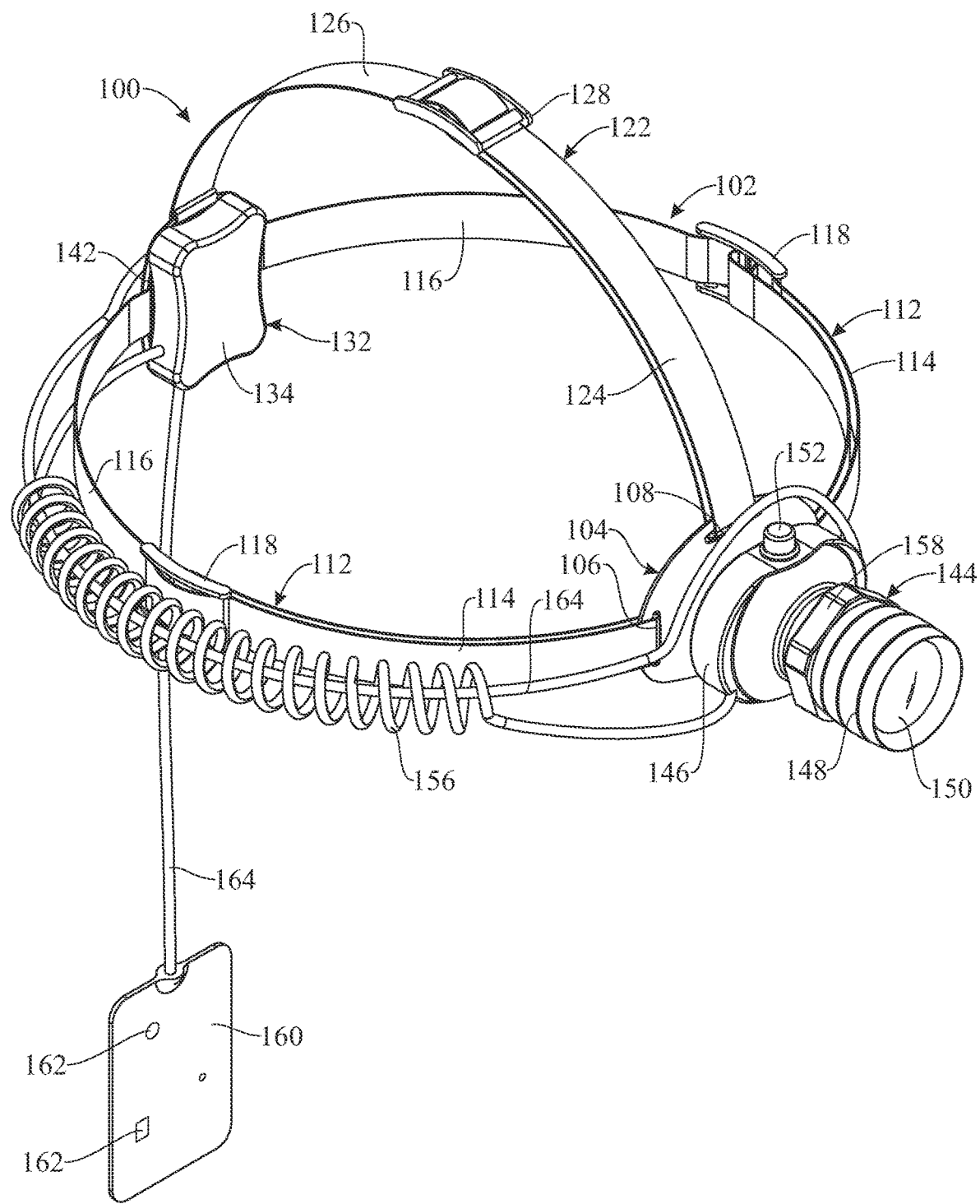
FIG. 1 presents a front perspective view of a surgical headlamp assembly in accordance with an illustrative embodiment of the present invention.

As illustrated in FIGS. 1 and 2, in some embodiments, the headpiece 102 may include a lamp mount panel 104. The lamp 144 may be supported by the lamp mount panel 104 such as by using bolts, brackets and/or other suitable techniques known by those skilled in the art.

The lateral strap members 112 and the upper strap member 122 of the headpiece 102 may be attached to the lamp mount panel 104 according to the knowledge of those skilled in the art. Accordingly, in some embodiments, a pair of side strap member slots 106 may extend through the lamp mount panel 104. The front lateral strap 114 of each lateral strap member 112 may loop through the corresponding side strap member slot 106. In like manner, an upper strap member slot 108 may extend through the lamp mount panel 104 between the side strap member slots 106. The front upper strap 124 may loop through the upper strap member slot 108.

As illustrated in FIGS. 1-3, in some embodiments, the battery pack 132 may be disposed behind and in spaced-apart relationship to the lamp mount panel, and the lateral strap members and the upper strap member of the headpiece may be secured to the battery pack.

As illustrated in FIG. 4, in some embodiments, at least one strap securement band 142 may secure the lateral strap members 112 and the upper strap member 122 of the headpiece 102 to the battery pack 132. The rear strap loop 120 which connects the rear lateral straps 116 of the lateral strap members 112 may extend between the parallel segments of the strap securement band 142.

As illustrated in FIGS. 1-3, in some embodiments, the lamp 144 may include a lamp housing 146. The light source (not illustrated) may be disposed in the lamp housing 146. In some embodiments, the light source may include at least one LED.

A lens housing 148 may extend from the lamp housing 146. At least one lens 150 may be disposed in the lens housing 148. In some embodiments, the lens 150 in the lens housing 148 may emit a focusable light beam 176 which can be conical (upper view in FIG. 7) or straight (lower view in FIG. 7). Accordingly, a light beam adjustment control 158 may be provided on the lens housing 148. The light beam adjustment control 158 may be configured to adjust the width of the light beam 176 emitted from the lens housing 148.

In some embodiments, a manual lamp button 152 may be provided on the lamp housing 146. The manual lamp button 152 may be configured to facilitate manual operation of the light source in the lamp housing 146 in emission of the light beam 176 from the lens housing 148.

As illustrated in FIG. 3, in some embodiments, the lamp 144 may be selectively adjustable at a selected angle with respect to the headpiece 102. Accordingly, at least one lamp hinge 154 may pivotally attach the lamp 144 to the lamp mount panel 104 of the headpiece 102. The lamp hinge 154 may facilitate vertical angular positioning of the lamp 144 to facilitate a selected trajectory of the light beam 176.

As illustrated in FIG. 4, the battery pack 132 may include a battery pack housing 134. At least one battery compartment 136 may be provided in the battery pack housing 134. At least one removable battery compartment cover 140 may close the battery compartment 136. A battery 138 may be insertable in each corresponding battery compartment 136 in the battery pack housing 134. The battery 138 may be rechargeable or disposable.

The lamp 144 may electrically interface with the battery pack 132 and with the lamp control module 160 via any technique which is suitable for the purpose. Accordingly, in some embodiments, battery wiring 156 may electrically connect the lamp 144 to the battery pack 132. Control wiring 164 may connect the lamp control module 160 to the lamp 144. As illustrated in FIGS. 1 and 2, the battery wiring 156 and the control wiring 164 may trail along one of the lateral strap members 112 of the headpiece 102.

As illustrated in FIG. 4, in some embodiments, the control wiring 164 may extend between the rear strap loop 120 and the battery pack housing 134 of the battery pack 132. Accordingly, as illustrated in FIGS. 1, 2 and 6, the lamp control module 160 may be deployable in a suspended configuration from the headpiece 102 in typical application of the lamp assembly 100.

As illustrated in FIGS. 5-7, in typical application of the headlamp assembly 100, the headpiece 102 may be placed on the head 170 of a wearer 168 with the lamp mount panel 104 of the headpiece 102 positioned in front of the forehead 172 of the user's head 170. In some applications, the wearer 168 may be a surgeon who desires to use the headlamp assembly 100 to illuminate a surgical field (not illustrated) during surgery. Accordingly, the lateral strap adjusters 118 and the upper strap adjuster 128 may initially be adjusted to lengthen the lateral strap members 112 and the upper strap member 122, respectively, and facilitate placement of the headpiece 102 on the wearer's head 170. The lateral strap members 112 and the upper strap member 122 may subsequently be shortened to tighten the headpiece 102 on the head 170. As illustrated in FIGS. 5 and 6, the control wiring 164 may be deployed from the battery pack 132 over the shoulder and in front of the chest of the wearer 168.

During the surgical procedure, the wearer 168 can contact the lamp controls 162 on the lamp control module 160 to selectively energize or deenergize the lamp 144 using his or her hand or arm. Accordingly, the light source (not illustrated) in the lamp 144 may emit the light beam 176 through the lens 150 in the lens housing 148 to illuminate the surgical field. The lamp controls 162 may in like manner be contacted to control the intensity and/or other parameters of the light beam 176. As illustrated in FIG. 7, the light beam adjustment control 158 may be manipulated to vary the conical (upper view) or straight (lower view) profile of the light beam 176. As illustrated in FIG. 3, the vertical angle of the lamp 144 with respect to the headpiece 102 may be adjusted via the lamp hinge 154 to direct the light beam 176 to the desired location or area. As illustrated in FIG. 4, the battery or batteries 138 can be periodically removed from the respective battery compartments 136 in the battery pack housing 134 of the battery pack 132 for recharging or replacement purposes. Due to the typically rear position of the battery pack 132 in the headpiece 102, in some applications, the batteries 138 can be quickly replaced by a nurse or other personnel during surgery.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A surgical headlamp assembly remotely actuatable at a wearer's chest and suitable for surgical applications, comprising:
   a headpiece sizable and configurable for placement on the head of the wearer;
   a lamp carried by the headpiece, the lamp including at least one light source;
   a battery pack including at least one battery carried by the headpiece, the lamp electrically interfacing with the at least one battery; and
   a remote lamp control module operationally interfacing with the at least one battery and the lamp, the lamp control module configured to control emission of a light beam from the lamp, the remote lamp control module suspendable from the headpiece and deployable in front of the chest of the wearer; and
   wherein the wearer may manipulate the lamp control module to energize and adjust the illumination intensity of the light beam without interruption of the surgical procedure and without the need to use the user's fingers.

2. The surgical headlamp assembly of claim 1, wherein the headpiece includes a plurality of headpiece straps.

3. The surgical headlamp assembly of claim 2, wherein the plurality of headpiece straps include a pair of lateral strap members and an upper strap member.

4. The surgical headlamp assembly of claim 3, wherein each of the lateral strap members and the upper strap member are selectively adjustable.

5. The surgical headlamp assembly of claim 2, wherein each lateral strap member includes a front strap, a rear lateral strap and a lateral strap adjuster between the front lateral strap and the rear lateral strap.

6. The surgical headlamp assembly of claim 2, wherein the upper strap member includes a front upper strap, a rear upper strap and an upper strap adjuster between the front upper strap and the rear upper strap.

7. The surgical headlamp assembly of claim 5, wherein a rear strap loop connects the rear lateral straps of the lateral strap members.

8. The surgical headlamp assembly of claim 3, wherein the headpiece includes a lamp mount panel, and further wherein the lamp is supported by the lamp mount panel and the lateral strap members and the upper strap member of the headpiece are attached to the lamp mount panel.

9. The surgical headlamp assembly of claim 8, wherein a pair of side strap member slots extend through the lamp mount panel, and the front lateral strap of each lateral strap member extends through the corresponding side strap member slot.

10. The surgical headlamp assembly of claim 9, wherein an upper strap member slot extends through the lamp mount panel between the side strap member slots, and the front upper strap loops through the upper strap member slot.

11. The surgical headlamp assembly of claim 8, wherein the battery pack is—disposed behind and in spaced-apart relationship to the lamp mount panel, and the lateral strap members and the upper strap member of the headpiece are secured to the battery pack.

12. The surgical headlamp assembly of claim 11, wherein at least one strap securement band is configured to secure the lateral strap members and the upper strap member to the battery pack.

13. The surgical headlamp assembly of claim 1, wherein the lamp includes a lamp housing, the lamp housing including at least one light source, the at least one light source including at least one LED, and further wherein the lamp housing is configured to emit a focusable light beam, the focusable light beam being either conical or straight.

14. The surgical headlamp assembly of claim 13, further comprising a lens housing extending from the lamp housing, the lens housing including at least one lens and a light beam adjustment control configured to adjust the width of the light beam emitted from the lens housing.

15. The surgical headlamp assembly of claim 1, the lamp is selectively adjustable at a selected angle with respect to the headpiece and at least one lamp hinge pivotally attaches the lamp to the headpiece.

16. The surgical headlamp assembly of claim 1, wherein the battery pack includes a battery pack housing and at least one battery compartment in the battery pack housing, and the battery is insertable in a battery compartment.

17. The surgical headlamp assembly of claim 1, further comprising a battery wiring connecting the lamp to the battery pack.

18. The surgical headlamp assembly of claim 17, the battery wiring trails along one of the lateral strap members of the headpiece.

19. A surgical headlamp assembly remotely actuatable at a wearer's chest and suitable for surgical applications, comprising:
 a headpiece sizable and configurable for placement on the head of the wearer, the headpiece including a plurality of headpiece straps, the plurality of headpiece straps including a pair of lateral strap members and an upper strap member, wherein the pair of lateral strap members and the upper strap member are selectively adjustable;
 a lamp carried by the headpiece, the lamp including at least one light source, the lamp including a lamp housing, the lamp housing including at least one light source, the at least one light source including at least one LED, wherein the lamp housing is configured to emit a focusable light beam, the focusable light beam being either conical or straight;
 a battery pack including at least one battery carried by the headpiece, the lamp electrically interfacing with the at least one battery; and
 a remote lamp control module operationally interfacing with the at least one battery and the lamp, the lamp control module configured to control emission of a light beam from the lamp, the remote lamp control module suspendable from the headpiece and deployable in front of the chest of the wearer and
 wherein the wearer may manipulate the lamp control module to energize and adjust the illumination intensity of the light beam without interruption of the surgical procedure and without the need to use the user's fingers.

20. A surgical headlamp assembly remotely actuatable at a wearer's chest and suitable for surgical applications, comprising:
 a headpiece sizable and configurable for placement on the head of the wearer, the headpiece including a plurality of headpiece straps, the plurality of headpiece straps including a pair of lateral strap members and an upper strap member, wherein the pair of lateral strap members and the upper strap member are selectively adjustable;
 a lamp carried by the headpiece, the lamp including at least one light source, the lamp including a lamp housing, the lamp housing including at least one light source, the at least one light source including at least one LED, wherein the lamp housing is configured to emit a focusable light beam, the focusable light beam being either conical or straight, and further wherein the lamp is selectively adjustable at a selected angle with respect to the headpiece and at least one lamp hinge pivotally attaches the lamp to the headpiece;
 a battery pack including at least one battery carried by the headpiece, the lamp electrically interfacing with the at least one battery, wherein the battery pack is disposed behind and in spaced apart relationship to the lamp mount panel, and further wherein the battery pack includes a battery pack housing and at least one battery compartment in the battery pack housing, and the battery is be insertable in a battery compartment; and
 a remote lamp control module operationally interfacing with the at least one battery and the lamp, the lamp control module configured to control emission of a light beam from the lamp, the remote lamp control module suspendable from the headpiece and deployable in front of the chest of the wearer and
 wherein the wearer may manipulate the lamp control module to energize and adjust the illumination intensity of the light beam without interruption of the surgical procedure and without the need to use the user's fingers.

* * * * *